United States Patent
Simanzhenkov et al.

(10) Patent No.: US 10,899,981 B2
(45) Date of Patent: Jan. 26, 2021

(54) METHOD FOR REMOVING FOULING DOWNSTREAM OF AN ODH REACTOR

(71) Applicant: NOVA Chemicals (International) S. A., Fribourg (CH)

(72) Inventors: Vasily Simanzhenkov, Calgary (CA); Shahin Goodarznia, Calgary (CA); Yoonhee Kim, Calgary (CA); Eric Clavelle, Calgary (CA)

(73) Assignee: NOCA Chemicals (International) S.A., Fribourg (CH)

( * ) Notice: Subject to any disclaimer, the term of this patent is extended or adjusted under 35 U.S.C. 154(b) by 0 days.

(21) Appl. No.: 16/186,873

(22) Filed: Nov. 12, 2018

(65) Prior Publication Data
US 2019/0177627 A1 Jun. 13, 2019

(30) Foreign Application Priority Data
Dec. 11, 2017 (CA) .................... 2988462

(51) Int. Cl.
| | |
|---|---|
| *C10G 75/00* | (2006.01) |
| *C10G 75/04* | (2006.01) |
| *C07C 5/333* | (2006.01) |
| *B08B 9/027* | (2006.01) |
| *B08B 9/032* | (2006.01) |
| *C07C 5/48* | (2006.01) |

(52) U.S. Cl.
CPC .............. *C10G 75/04* (2013.01); *B08B 9/027* (2013.01); *B08B 9/032* (2013.01); *B08B 9/0321* (2013.01); *C07C 5/333* (2013.01); *C07C 5/48* (2013.01); *C10G 2300/1081* (2013.01); *C10G 2300/4075* (2013.01); *C10G 2300/44* (2013.01); *C10G 2300/805* (2013.01); *C10G 2400/20* (2013.01)

(58) Field of Classification Search
CPC ........... C07C 5/48; C07C 11/04; C07C 5/333; C10G 2300/1081; C10G 2300/4075; C10G 2300/44; C10G 2300/805; C10G 2400/20; C10G 75/04; A63H 1/02; B08B 9/027; B08B 9/032; B08B 9/0321; F16L 2101/12; F16L 55/38
See application file for complete search history.

(56) References Cited

U.S. PATENT DOCUMENTS

| | | |
|---|---|---|
| 3,531,541 A | 9/1970 | Woerner |
| 3,728,413 A | 4/1973 | Woerner |
| 4,773,357 A | 9/1988 | Scharton et al. |
| 7,279,052 B2 | 10/2007 | Kinnari et al. |
| 10,308,569 B2 * | 6/2019 | Josch ............... C07C 7/005 |

FOREIGN PATENT DOCUMENTS

WO 2013/169679 A1 11/2013

OTHER PUBLICATIONS

Oliemans, R.V.A. and Pots, B.F.M.; Gas-Liquid Transport in Ducts; Multiphase Flow Handbook; Edited by Clayton T. Crowe; copyright 2006 by Taylor & Francis Group, LLC, Chapter 2, pp. 2.1-2.40.

* cited by examiner

*Primary Examiner* — Sharon Pregler
(74) *Attorney, Agent, or Firm* — Thomas J. Styslinger (57) ABSTRACT

A method for preventing or removing water soluble fouling located downstream of an oxidative dehydrogenation (ODH) reactor is described. The method employs the introduction of water upstream of fouling locations, either continuously or intermittently, which acts to solubilize and carry away fouling material. The method has the advantage of being applicable for use while an ODH process is ongoing, circumventing the need for a costly shutdown.

20 Claims, 4 Drawing Sheets

METHOD FOR REMOVING FOULING DOWNSTREAM OF AN ODH REACTOR

This present disclosure relates to the use of reactors for oxidative dehydrogenation (ODH) of lower (C2-4) paraffins into corresponding olefins. More specifically, the present disclosure relates to a method for preventing and or removing fouling in the output line of an ODH reactor.

Catalytic oxidative dehydrogenation (ODH) of ethane into ethylene has been known for some time as an alternative to thermal cracking, but has not been commercially accepted due to safety concerns of mixing a hydrocarbon with oxygen and the infusion of capital required to replace familiar facilities that despite being costly to run, are reliable and display very high conversion rates. In recent years numerous ODH related patents have been published or granted in relation to improving safety or increasing efficiency using mixed metal oxide catalysts that have higher conversion and selectivity rates. In contrast, there has been little discussion on the operation and maintenance of ODH reactors that will significantly impact cost efficiency should ODH gain commercial acceptance. ODH is exothermic in nature and, in contrast to thermal cracking, does not require furnaces that produce coking, not to mention vast amounts of greenhouse gases. The advantage for ODH is that it is not associated with unavoidable, time consuming and costly delays characteristic of coke removal.

Like many oxidative processes ODH will require monitoring and control of reactor conditions, variation of which can impact yields and the degree to which unwanted byproducts are produced. For example, ODH reaction conditions can impact what type and how much of oxygenates, such as acetic and maleic acid, are present in the off stream from the reactor. Downstream separation of reaction products is a given, with operators altering conditions so as to promote formation of some products while avoiding others which require more costly efforts for separation. Downstream separation requires cooling which unfortunately may have the undesired effect of fouling when water soluble components, like maleic acid, condense and then freeze, finally adhering to the reactor infrastructure. If this were to occur the advantage ODH holds over thermal cracking in relation to shutdown may be negated.

For the petrochemical industry in general, fouling or plugging of pipes and equipment is a common problem, with solutions for dealing with the problem including chemical and mechanical treatments. For example, oil and gas pipelines accumulate deposits of solids that necessitate periodical shutdowns for cleaning, various methods for which are present in the prior art. One example, WIPO application 2013/169679 filed May 7, 2013 in the names of Fisher et. al., applicant M-I L.L.C, teaches a method for cleaning a natural gas pipeline by introducing a cleaning fluid that comprises a diluent selected from glycol, glycerin, or mixtures thereof. The patent teaches using the selective diluents because use of water in natural gas pipelines is not recommended as it can lead to the formation of muds, rust and hydrate plugs.

The prior art also includes various methods for removing hydrate plugs from oil and gas pipelines. The plugs can be removed by depressurization, chemical injection, or heating. Also, mechanical removal using a thruster pig as taught in U.S. Pat. No. 7,279,052 issued Oct. 9, 2007 to Kinnari et. al., assigned to Statoil Asia and Crawford Technical Services, Inc., is known. In this instance deposits are removed continuously or intermittently as the pig is advanced with the help of a thrusting fluid and return flow line.

The solutions for removing plugging in oil and gas pipelines, while informative, are not necessarily practical when applied to the problem of plugging immediately downstream of an ODH reactor. Oil and gas pipelines comprise a significantly larger diameter and cover much longer distances, and are averse to use of water for cleaning. For oxidative processes, the equipment, including piping and associated components, are much smaller in scale and not susceptible to the type of moisture damage commonly avoided in the oil and gas industry.

Using water to remove fouling in industrial plant components has been described in the art. U.S. Pat. No. 4,773,357 issued Sep. 27, 1998 to Scharton et. al., assigned to Anco Engineers, Inc., teaches a method for cleaning a tube sheet of a heat exchanger using a water cannon. Nuclear power reactors comprise a large number of heat exchangers that experience the buildup of sludge at the bottom end. The sludge includes copper oxides, magnetite, and products of corrosion, oxidation, and other sedimentation. The patent teaches that the sludge found on the tube sheet can be dislodged by explosive discharging of water, optionally with a directional nozzle, on to the sludge. Unfortunately, the method requires shut down of the heat exchanger.

U.S. Pat. No. 3,531,541 issued Sep. 29, 1970 to Woerner, assigned to Petro-Tex Chemical Corporation teaches reducing of fouling of compressor pistons and cylinders used for compression of gaseous compositions, preferably produced in an oxidative dehydrogenation process. The process was designed to clean out fouling believed to comprise oxygenated and/or unsaturated organic compounds that adhere to contact surfaces following compression. The patent teaches spraying water into the suction side of the compressor where the gaseous composition, preferably exclusive of water, is introduced.

U.S. Pat. No. 3,728,413, issued Apr. 17, 1973 to Woerner, assigned to Petro-Tex Chemical Corporation teaches reducing of fouling of compressors downstream of an oxidative dehydrogenation process. Risk of fouling due to polymeric compounds formed from precursors during compression is mitigated by removing precursors with water. The process teaches removal of water from effluent from an oxidative process during a cooling step, then reintroduction of water before or during compression, and followed up with a scrubbing step to remove the impurities. The patent does not teach removal of water soluble fouling immediately downstream of a reactor and prior to quenching and compression.

Provided herein is a method for removing or preventing buildup of water soluble fouling that accumulates downstream of an ODH reactor used for oxidative dehydrogenation of lower paraffins into corresponding olefins. In one embodiment, a solvent is introduced into the outlet pipe from the ODH reactor upstream of where fouling is likely to develop, primarily in a liquid state and in a manner that promotes annular flow, laminar or turbulent, of solvent along the inner surface of the pipe immediately downstream of the location of introduction. In one embodiment the solvent introduced into the outlet pipe is water.

In another embodiment, solvent is introduced via a pipe-in-pipe arrangement, with the outlet pipe from the reactor fitting within a downstream pipe that has a larger diameter. In this instance solvent is introduced by way of the gap between the outlet pipe and the downstream pipe.

In another embodiment solvent can be sprayed onto the inner surface of the outlet pipe by an instream atomizer, or alternatively by a series of jets strategically placed on and continuous with the inner surface of the outlet pipe.

In another embodiment solvent is introduced via a plurality of holes with exits continuous with the inner surface of the outlet pipe.

In a further embodiment water is introduced via a pipe-in-pipe arrangement in combination with instream atomizers, inner surface jets, a plurality of holes, or combinations thereof.

Other than in the operating examples or where otherwise indicated, all numbers or expressions referring to quantities of ingredients, reaction conditions, etc. used in the specification and claims are to be understood as modified in all instances by the term "about". Accordingly, unless indicated to the contrary, the numerical parameters set forth in the following specification and attached claims are approximations that can vary depending upon the properties that the present invention desires to obtain. At the very least, and not as an attempt to limit the application of the doctrine of equivalents to the scope of the claims, each numerical parameter should at least be construed in light of the number of reported significant digits and by applying ordinary rounding techniques.

Disclosed herein is a method for removing of and or preventing buildup of substantially water soluble fouling in the outlet pipe of an oxidative dehydrogenation (ODH) reactor used for converting lower paraffins (C2-C4) into corresponding olefins. The term "fouling", including in the worst case "pluggage", refers to water soluble by-products of an ODH process that solidify after leaving the reactor and have the potential to adhere to and build up on the interior surface of the outlet pipe leaving the ODH reactor. Left unchecked the fouling can limit or even block flow through the exit pipes, impacting the efficiency of the ODH process. Pluggage refers to complete occlusion of the pipe. Water soluble by-products of the ODH process include oxygenates, such as maleic acid. The modifier "substantially water-soluble" refers to the possibility that fouling may also include minor amounts of miscible products such as acetaldehyde and ethanol, or other non-soluble particulate entrained within the solid fouling. Lower paraffins refer to paraffins with 2 to 4 carbons. In one embodiment the lower paraffin is ethane and its corresponding olefin is ethylene. For simplicity the method is described for use with ethane ODH, but may be applied to use of propane and butane ODH.

An advantage of the disclosed method is that fouling can removed or prevented from forming while the ODH reactor is operational. Operational means during operation, as opposed to periods of shut-down where the reactor is idle and flow of reactant and product gases has stopped. Shut-downs are potentially time consuming and costly. The method disclosed reduces the risk of a need for shut-down, which has significant economic implications. However, the method may also be employed during reactor shut-down. In this instance, the volumes and flow rates of solvent introduced would be need to be varied accordingly.

Figure 1:
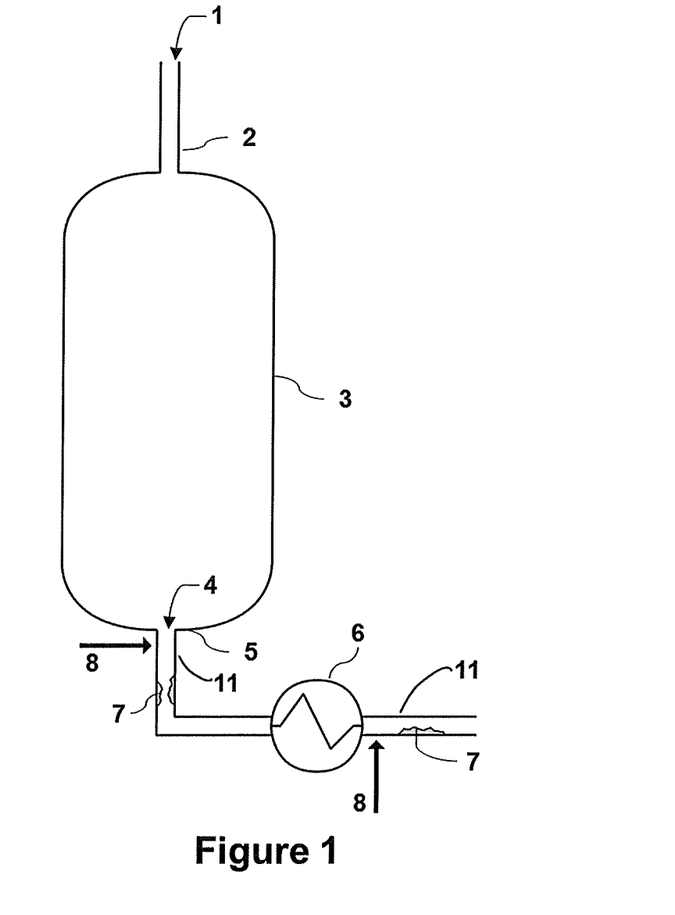
FIG. 1—Schematic of ODH reactor and associated downstream piping showing where fouling may develop.

The method described is intended for use in relation to an ODH process wherein a gas mixture 1 comprising at least ethane and oxygen is introduced, via one or more inlets 2, into an ODH reactor 3 that contains an ODH catalyst (FIG. 1). Conditions within the ODH reactor 3 promote conversion of ethane into ethylene. The oxidative reaction catalyzed by the ODH catalyst may produce a variety of byproducts, for example carbon dioxide, acetic acid, and water soluble oxygenates such as maleic acid. Exit stream 4 comprising ethylene and by-products, and any unreacted ethane and oxygen, if present, exit ODH reactor 3 via outlet pipe 5. Temperature of the exit stream 4 may vary and is controlled by an operator depending upon desired reaction conditions which are tailored for a specific target product profile. Upon exiting the ODH reactor 3, the exit stream 4 in the absence of exothermic reaction conditions begins cooling naturally and optionally with the aid of cooling mechanisms, such as heat exchanger 6, before being subjected to a series of separation steps, starting with for example a quench tower for removal of water and acetic acid.

Without wishing to be bound by theory, as the temperature of exit stream 4 drops, water soluble oxygenates, present in the gaseous state within ODH reactor 3, condense within the gaseous exit stream 4 as liquid droplets, then adhering to inner surface of outlet pipe 5, eventually solidifying as fouling 7 in one more locations downstream of ODH reactor 3 and upstream of where separation steps begin. While the fraction of exit stream 4 that has water soluble oxygenates is minimal, without intervention fouling 7 may grow over time as more particles of solid water soluble oxygenates adhere to the growing mass. Growth of fouling 7 may be detected as an atypical pressure drop between the reactor and a location downstream of outlet pipe 5. Introduction of a solvent at one or more locations (arrows 8) upstream of the location of the fouling promotes dissolving of the fouling 7, which can then be carried by the flow of gases and liquids to the separation steps, where it can be removed along with acetic acid.

The ODH Reactor

The disclosed method contemplates the use of any of the known reactor types applicable for the ODH of hydrocarbons. In some embodiments the method disclosed herein employs one or more conventional fixed bed reactors. In a typical fixed bed reactor reactants are introduced into the reactor at one end, flow past or over an immobilized catalyst, products are formed and leave at the other end of the reactor. The reactor may include separate inlets for each of the reactants, or may include a single inlet (similar to FIG. 1) where reactants are premixed and introduced into the reactor as a homogeneous mixture. A person skilled in the art would know which features are required with respect to shape and dimensions, inputs for reactants, outputs for products, temperature and pressure control and monitoring, and means for immobilizing the catalyst.

In another embodiment, use of one or more fluidized bed reactors is contemplated. These types of reactors are well known. Typically, the catalyst is supported by a porous structure, or distributor plate, located near a bottom end of the reactor and to which reactants are forced through at a velocity sufficient to balance the weight of the catalyst such that it rises and begins to swirl around in a fluidized manner. The reactants are converted to products upon contact with the fluidized catalyst and subsequently removed from the upper end of the reactor. Design considerations include shape of the reactor and distributor plate, input and output, and temperature and pressure control and monitoring, all of which would fall under knowledge of the person skilled in the art.

Another embodiment contemplates using multiple ODH reactors, either in series or in parallel. Use of multiple reactors, including ODH reactors, in either a parallel or series arrangement is well known in the art. Where parallel ODH reactors are employed, the method disclosed herein may be used downstream of each of the ODH reactors, after streams from each of the ODH reactors are combined, or both downstream of each of the ODH reactors and after streams of each of the ODH reactors are combined.

Where ODH reactors in series are employed fouling would not be expected between ODH reactors as the temperature is not likely to drop far enough such that condensation and freezing of oxygenates can occur. In some embodiments, it may be preferable that introduction of solvent for prevention or removal of fouling is only used downstream of the last ODH reactor in the series. However, if fouling is seen between ODH reactors, the method of the present disclosure may be used between ODH reactors in series, but a user should ensure that when using water as the solvent, that water introduced between ODH reactors is either removed prior to the next ODH reactor in the series, or that the temperature of the stream is high enough to convert the water into steam prior to entering the next ODH reactor. Liquid water within an ODH reactor is potentially damaging to the catalyst and the reactor and associated components.

The ODH Process

Use of an ODH reactor as applied to the present disclosure falls within the knowledge of the person skilled in the art. The oxidative dehydrogenation of ethane may be conducted at temperatures from 300° C. to 550° C., or from 300° C. to 500° C., or from 350° C. to 450° C., at pressures from 0.5 to 100 psi (3.447 to 689.47 kPa), or from 15 to 50 psi (103.4 to 344.73 kPa), and the residence time of the lower alkane in the reactor is, for example, from 0.002 to 30 seconds, or from 1 to 10 seconds.

Any of the ODH catalysts known in the art are suitable for use with the method disclosed herein. When choosing a catalyst a skilled user would appreciate that catalysts can vary with respective to selectivity and activity. In one embodiment, mixed metal oxides are employed as they can provide high selectivity to ethylene without significant loss in activity. Example catalysts are those of the formula:

$$V_a Mo_b Nb_c Te_d Me_e O_f$$

wherein: Me is a metal chosen from Ta, Ti, W, Hf, Zr, Sb and mixtures thereof; a is from 0.1 to 3; b is from 0.5 to 1.5; c is from 0.001 to 3; d is from 0.001 to 5; e is from 0 to 2; and f is a number to satisfy the valence state of the catalyst.

A wide variety of combinations for ratios of ethane, oxygen, and optionally inert diluent, can be used in the ODH process. A person skilled in the art would understand that for safety reasons, it may be preferable to choose those compositions where the ratio of oxygen to ethane, in the presence or absence of inert or substantially inert components, falls outside of the flammability envelope. This includes ratios either above the upper flammability limit or below the lower flammability limit. A person skilled in the art would know how to determine flammability limits, and whether a particular composition, including those that include an inert diluent, would fall outside of the flammability envelope.

Oxygen may be supplied as pure oxygen, or as a component of a gas mixture such as atmospheric air. Atmospheric air contains nitrogen, which acts as an inert diluent. If using pure oxygen and an inert diluent, the inert diluent should exist in the gaseous state in the conditions within the reactor and should not increase the flammability of the hydrocarbon added to the reactor, characteristics that a skilled worker would understand when deciding on which inert diluent to employ. Inert diluent can be added to either of the ethane or oxygen, or oxygen containing gas if using, prior to entering the ODH reactor or may be added directly into the ODH reactor.

The reaction conditions and reactant compositions, including ratio of ethane to oxygen, and the presence, absence or nature of inert diluent, along with the catalyst employed can impact the product profile, including the selectivity to ethylene, the conversion rate, and the degree that oxygenates, such as maleic acid, are produced in the ODH reaction. A person skilled in the art would be familiar with how adjusting conditions and components impact the product profile. Detecting the presence of fouling, requiring the need for removal, is achieved by monitoring the pressure drop as exit stream 4 leaves the reactor. Under normal operating conditions the pressure will drop along with the temperature. When fouling starts to develop it may begin to occlude the pipes downstream of the ODH reactor, resulting in a change in the pressure profile. Pressure upstream of the fouling will be higher than normal while pressure downstream of the fouling will be lower than what occurs under normal circumstances. A complete blockage would likely result in a very large pressure increase upstream of the fouling. A larger than normal pressure drop would be expected when there is higher than normal pressure upstream of the fouling and lower than normal pressure downstream of the fouling.

Introduction of Solvent

Solvents that can be used in accordance with the described method are those that can dissolve the substantially water soluble fouling, exist in liquid form at the temperature and pressure found in outlet pipe 5 downstream of the ODH reactor, and do not negatively impact downstream separation steps. In some embodiments the solvent is water. Water used with the method need not be distilled or deionized, and can include some impurities, provided the impurities are non-reactive with respect to olefins and are not likely to negatively impact downstream processing. Collection water from the bottom of an acetic acid scrubber, which is likely the first separation unit downstream of the ODH reactor, may also be used as the solvent. Collection water from the bottom of an acetic acid scrubber may be described as dilute acetic acid, with the concentration of acetic acid ranging from 0-50 wt. %, for example from 1 to 10 wt. %. Using dilute acetic acid has the advantage of recycling water used in the acetic acid scrubber so that an additional water source may not be required. Embodiments of the disclosed method will be described using water as the solvent. In each instance, the solvent need not be water but any other substance that can dissolve the substantially water soluble fouling, exists in primarily liquid state in the prevailing conditions, and does not negatively impact downstream processing.

Introduction of water downstream of the ODH reactor and upstream of fouling can be done in multiple locations prior to the separation steps. The water introduced is primarily in the liquid state at the temperature and pressure where it is introduced. In liquid form water has the capability of dissolving the substantially water-soluble fouling, while as a steam this is not possible. Introduction of water is performed so that an annular flow of water, denoted by dashed curved arrows in FIGS. 2-5, substantially on the inner surface of the pipe contacts and begins to dissolve fouling 7, carrying fouling particles 9 away from the side of the pipes (FIG. 2).

Figure 2:
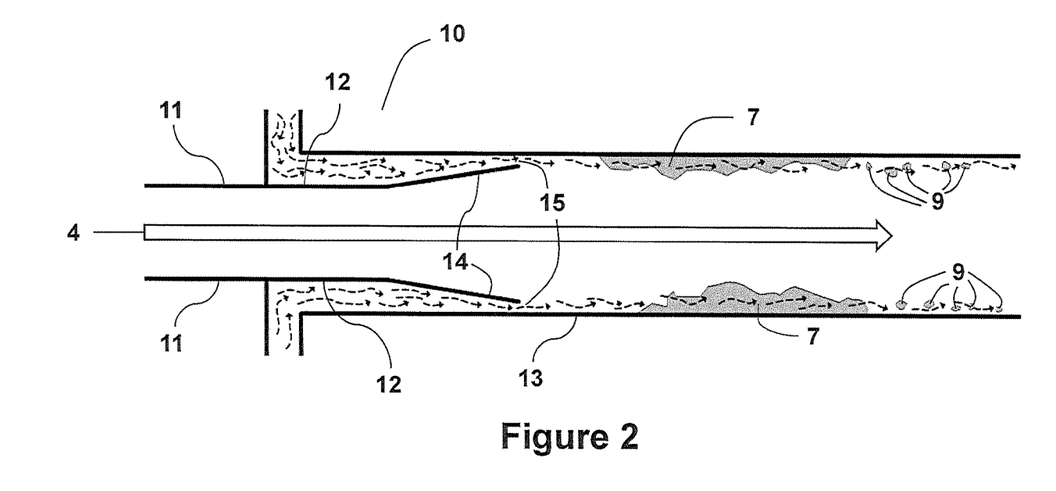
FIG. 2—A side view of a pipe-in-pipe arrangement according to an embodiment of the present invention.
Figure 3:
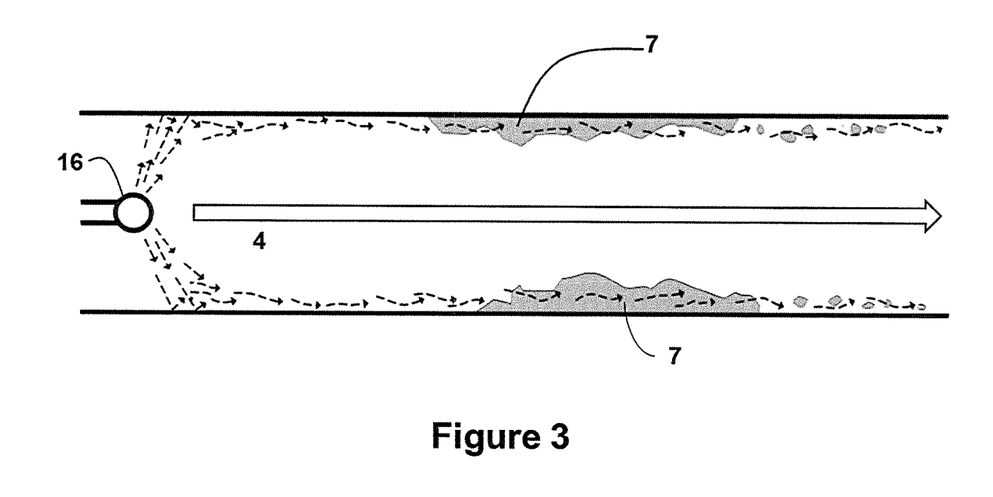
FIG. 3—A side view of the outlet pipe with an instream atomizer according to an embodiment of the present invention.

In one embodiment, as shown in FIG. 2, a pipe in pipe arrangement 10 can be used to deliver the water in the desired manner. In this arrangement pipe 11 coming from and continuous with outlet pipe 5 or an outlet pipe downstream from a cooling mechanism (e.g. heat exchanger 6)(FIGS. 1 and 2) becomes an inner pipe 12, ending and fitting inside an outer pipe 13 with a larger diameter. The end of inner pipe 12 may or may not have a flare 14, so long as there is a gap 15, continuous or discontinuous, between the internal surface of outer pipe 13 and the terminal end of inner pipe 12, where water can be introduced. The gap is chosen such that the water preferentially films on the internal surface of outer pipe 13, producing what is often referred to as annular flow. Inner pipe 12 may also include rifling to produce swirling of the water as it is introduced, promoting complete coverage of the internal surface of outer pipe 13. The end of inner pipe 12 should be located in positions upstream of where fouling may develop. Multiple pipe in pipe arrangements 10 can be used in multiple locations. The outer pipe 13 of an upstream pipe in pipe arrangement 10 acts like the inner pipe 12 for the subsequent pipe in pipe arrangement 10. A user may choose to taper the diameter of outer pipe 12 as it approaches the next arrangement, or may choose an inner pipe 12 with a consistent diameter. In this case, the diameter of each subsequent outer pipe 13 increases.

Figure 4A:
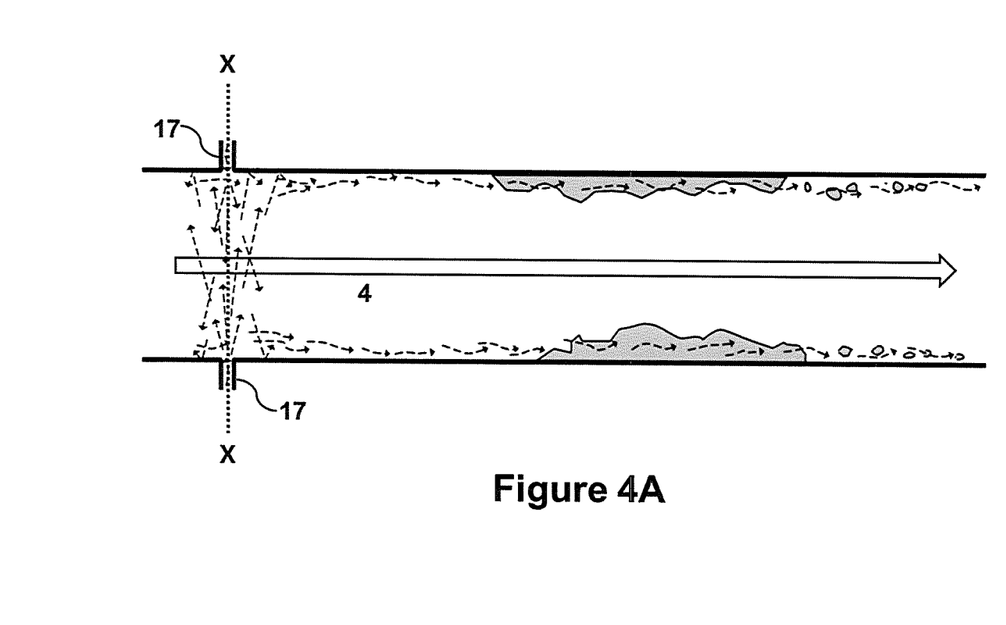
FIG. 4A—A side view of the outlet pipe with inner surface jets according to an embodiment of the present invention.
Figure 4B:
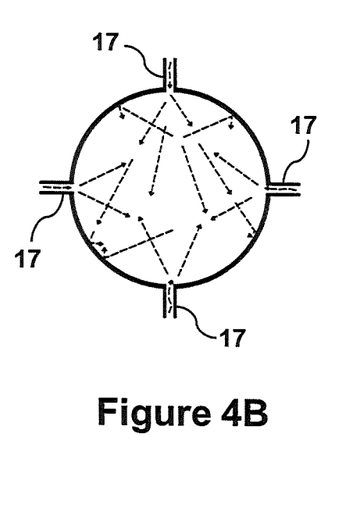
FIG. 4B—Cross-sectional view of the outlet pipe with inner surface jets of FIG. 4A along line X-X.

In another embodiment, water may be introduced via an instream atomizer head 16 (FIG. 3), the atomizer spraying the interior walls from a position within the stream of reactants leaving the ODH reactor. In another embodiment, water may be introduced using of multiple jets 17 within the walls of the exit pipe 11 (FIGS. 4A and 4B). Jets 17 may spray an area of the inner wall (indicated by straight dashed arrows) of the pipe opposite the jet, the size of the area depending on the configuration of the nozzle on the end of the jet 17. The use of multiple jets can be used to ensure coverage of the inner wall of the exit pipe 11, the number required depending on the nozzle and the spray area of the jets (see cross section of pipe with jets in FIG. 4B). The jets may be in a concentric circle, or can be staggered with some jets further upstream of subsequent jets.

Figure 5A:
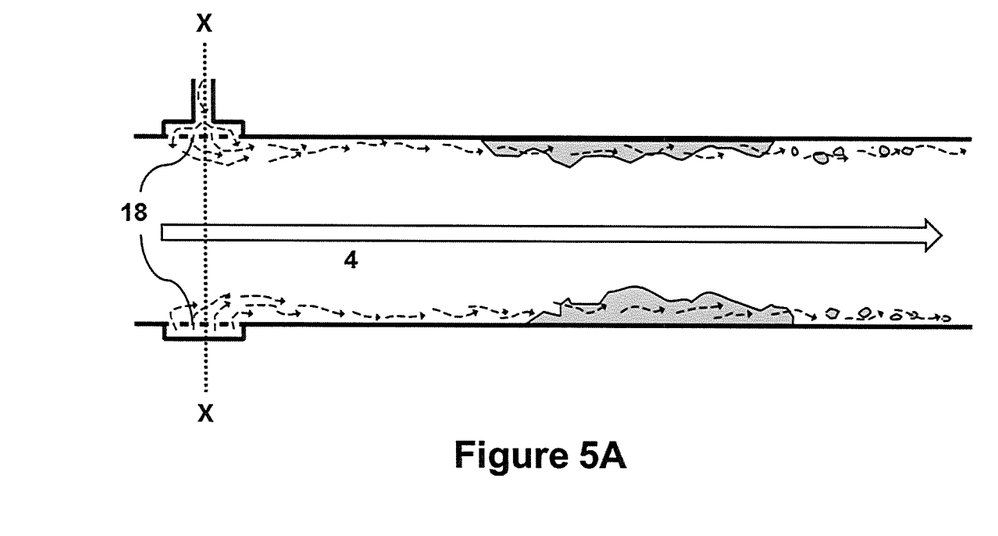
FIG. 5A—A side view of the outlet pipe with a plurality of holes according to an embodiment of the present invention.
Figure 5B:
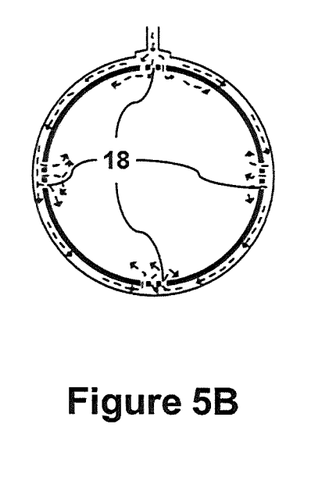
FIG. 5B—Cross-sectional view of the outlet pipe with a plurality of holes of FIG. 5A along line X-X.

In another embodiment, water (indicated by curved dashed arrows) can be introduced via a plurality of holes or perforations 18 on the inner surface of the pipe where the water is introduced (FIGS. 5A and 5B). The holes would be designed to allow water to leak or seep into the pipe, including an option for closing the holes and for controlling the flow of water through the holes to promote annular flow once inside the pipe. Designs of this type fall within the knowledge of the person skilled in the art. Perforations or holes 18 can be spaced in a uniform pattern or may dispersed at various locations lengthwise along exit pipe 11.

The embodiments for introduction of water are not intended to solely be used in isolation. In another embodiment, introduction of water can be done at one or more locations, with each location employing one or more ways for introducing water into the pipe. For example, a pipe in pipe arrangement may be used in conjunction with an instream atomizer, or perforations, or multiple jets. In using multiple ways for introduction of water into the pipe a user must be mindful that increasing the amount of introduced water may dilute the stream more than when using a single way of introducing water.

The introduction of water into pipes downstream of the reactor wherein there is a gaseous flow creates a multiphase flow arrangement, made up of the gaseous exit stream 4 and introduced liquid water. A person skilled in the art would be familiar with a variety of mechanisms for introducing water at appropriate flow rates such that an annular flow of water develops substantially at the inner surface of the pipe (i.e. on or near the surface of the pipe as depicted in FIGS. 2, 3, 4a and 5a). Factors to consider when determining flow rates of water to be introduced include the flow rate, temperature, and pressure of exit stream 4 coming off the ODH reactor 3. Flow rate of the gaseous exit stream 4 will be dependent on the size of the ODH reactor and can range from 2 L/min for bench scale up to 80,000 L/min for commercial scale reactors. The temperature and pressure will depend upon reactor configuration and reaction conditions discussed previously. Both temperature and pressure, in the absence of fouling, beginning falling immediately after exiting the reactor.

Choosing flow rates should also take into account the degree to which the water begins to dilute the exit stream. A user needs to determine the appropriate flow rate that permits formation of an annular stream without adding too much water that will need to be removed downstream. In some embodiments it may be preferable for removal of water to be done during a quench step that also separates out acetic acid produced. Introduction of copious amounts of water into the exit stream will add to that used in the quench step, diluting the acetic acid further. A user that further concentrates the acetic acid after separation may wish to limit the amount of water added for preventing fouling so as to reduce the degree to which the acetic acid needs to be concentrated.

Water is introduced into the pipe under conditions of gaseous flow through the pipe that will result in annular flow of liquid. Formation of an annular flow of liquid for a given gaseous flow rate is a function of gaseous and liquid densities, viscosities, surface tension, and flow rate. For more information on factors related to multiphase flow see Chapter 2, "Gas-Liquid Transport in Ducts", of the Multiphase Flow Handbook by Clayton T. Crowe, 2006.

In limited circumstances, a brief slug flow could be used. Brief means a short enough period of time to not disrupt reactor operations, such that the reactors needs to be shut down. In this instance, the volume of water introduced into the pipe is high enough to form "slugs" of liquid water, preceded and followed by pockets of gaseous flow. As the slugs move downstream fouling is dislodged from the interior surface of the pipe by the passing slug of water, and dissolves as the slug moves along. If introduction of water at higher volumes associated with slug flow is maintained then pressure within the reactor may increase to a point where reaction conditions are not ideal. This should be avoided. Also, downstream separation units must be capable of withstanding any sudden pressure increase resulting from interaction with voluminous slugs of water.

Choosing a location for introduction of water requires consideration of where fouling develops or is likely to develop. These locations are generally expect to occur where the temperature and pressure are conducive to water soluble oxygenates forming solid particulate that can adhere to the inner surface of the piping connecting the reactor with downstream separation components. For instance, the melting point of maleic acid is 135° C. at ambient pressure. Using a temperature profile of the exit stream as it leaves the reactor would provide a guide where water can be introduced, ideally at a location where the temperature exceeds the melting point of maleic acid. However, a user would understand that locations should be chosen where the introduced water is unlikely to boil to a significant degree or the water dissolves the fouling faster than it boils. In some embodiments, the introduced water remains substantially in the liquid state until it dissolves the fouling. The temperature of the water after introduction will likely increase, depending on location of introduction and temperature of water at location of introduction, peak and then decline as the stream gets further downstream. The location of introduction may therefore include locations above the boiling point of water, provided the flow rates allow that the peak temperature of introduced water to remain below boiling allowing it to remain in the liquid state for the time required to dissolve the foulant.

Intermittent or Consistent Operation

The method disclosed herein may be employed continuously or intermittently. That is, water may be introduced at one or more locations continuously during operation of the ODH reactor. In this instance a user may opt for the lowest possible flow rate of water to minimize the degree to which the product stream is diluted. Continuous operation may be effective for preventing fouling from forming in the first place as the interior surface of the piping downstream of the reactor and prior to separation components is constantly covered with a film of flowing water. The fouling particles are not subjected to conditions where adherence can be maintained for a period long enough that subsequent particles can adhere to the previous particles which would allow the mass to grow.

Alternatively, a user may opt to employ a method of the present disclosure when it is deemed prudent. The operating conditions may be such that water soluble byproducts are produced at such a low level that accumulation of fouling takes a long time to develop. When a user determines that the pressure drop from the reactor is outside a normal range expected in the absence of fouling the method may be used and water can be introduced into or more locations of the user's choosing. When the pressure drop returns to normal introduction of water into the stream can be ceased. Pressure transducers placed in intervals downstream of the reactor can pinpoint where fouling is accumulating by highlighting those sections where there is an abnormal pressure drop. A user may then opt to introduce water at a location just upstream of the fouling, or multiple locations. If the pressure drop does not correct over time a user may then increase the amount of water added, or the number of locations upstream where water is added. Alternatively, a user may opt for introduction of water such that slug flow is used. Finally, if given sufficient time and the pressure drop does not improve it may indicate that a problem involving fouling that is not water soluble is occurring.

EXAMPLES

Two fixed bed reactors, connected in series, were used in an ODH process where ethane, ethylene, carbon dioxide, and oxygen, in ratios of 11-93/0-80/0-8/0-8 vol %, respectively, were premixed before being fed to the first of the two reactors. The weight hourly space velocity was within the range of 0.65 to 2.70 $h^{-1}$. Output from the first reactor was sent directly into the second reactor without addition of new reactants. For each reactor, the temperature was held in the range of 300-337° C. at ambient pressure. The process was run continuously over a period of forty three days, with feed composition varying within the stated ranges. An abnormal pressure profile was detected immediately downstream of the second reactor and prior to a downstream condenser. The process was stopped due to triggering of the high pressure alarm for the reactor and the outlet line from the second reactor was disconnected. Upon inspection fouling was detected, the foulant occluding approximately 40% of the cross section of the pipe. Analysis of the foulant using GC-MS identified maleic acid/anhydride as the main probable component(s)(>90%) with smaller amounts of acetic acid, and a trace amount of 1,2-benzene dicarboxylic acid. The fouling was cleared almost immediately upon passing water through the pipe. The results show that foulant can be removed with water and that a person skilled in the art familiar with multiphase flow arrangements would be able to design inputs for introduction of water into piping downstream of an ODH reactor in the fashion described by the method disclosed herein.

What is claimed is:

1. A method for the oxidative dehydrogenation of ethane to ethylene comprising removing or preventing buildup of substantially water soluble fouling in the piping downstream of an idle or operational ODH reactor, comprising introducing a solvent into one or more locations within the piping, with at least one of the one or more locations at a position upstream of fouling, and wherein the solvent is introduced primarily in a liquid state at the pressure and temperature within the piping at the location of introduction.

2. The method of claim 1, wherein the solvent is introduced at a flow rate or pressure that promotes an annular flow of solvent substantially in contact with the inner surface of the piping.

3. The method of claim 1, wherein the ODH reactor is operational and the solvent is introduced at a flow rate or pressure that promotes slug flow of the solvent and wherein the introduction of the solvent does not disrupt operation of the ODH reactor.

4. The method of claim 1, wherein the solvent is water.

5. The method of claim 2, wherein the solvent is water.

6. The method of claim 3, wherein the solvent is water.

7. The method of claim 1, wherein the solvent is dilute acetic acid.

8. The method of claim 2, wherein the solvent is dilute acetic acid.

9. The method of claim 3, wherein the solvent is dilute acetic acid.

10. The method of claim 1, wherein the solvent is introduced into at least one of the one or more locations via a pipe in pipe arrangement.

11. The method of claim 10, wherein the solvent is water.

12. The method of claim 10, wherein the solvent is dilute acetic acid.

13. The method of claim 1, wherein the solvent is introduced into at least one of the one or more locations via an instream atomizer.

14. The method of claim 13, wherein the solvent is water.

15. The method of claim 13, wherein the solvent is dilute acetic acid.

16. The method of claim 1, wherein the solvent is introduced by a plurality of holes around the circumference of the pipe.

17. The method of claim 16, wherein the solvent is water.

18. The method of claim 16, wherein the solvent is dilute acetic acid.

19. The method of claim 1, wherein the solvent is introduced into at least one of the one or more locations continuously during operation of the ODH reactor.

20. The method of claim 1, wherein the solvent is introduced into at least one of the one or more locations intermittently during operation of the ODH reactor.

* * * * *